United States Patent [19]

Paulos

[11] Patent Number: 5,314,696
[45] Date of Patent: May 24, 1994

[54] METHODS FOR MAKING AND ADMINISTERING A BLINDED ORAL DOSAGE FORM AND BLINDED ORAL DOSAGE FORM THEREFOR

[76] Inventor: Manley A. Paulos, 15626 Cold Spring Ct., Granger, Ind. 46530

[21] Appl. No.: 722,155

[22] Filed: Jun. 27, 1991

[51] Int. Cl.$^5$ ............................................. A61K 9/48
[52] U.S. Cl. ......................................... 424/453; 424/451;
424/463; 424/475; 428/7; 428/15; 428/35.6
[58] Field of Search ............... 424/463, 475, 451, 453;
428/7, 15, 35.6; 604/890.1, 892.1; D24/100,
101, 104

[56] References Cited

U.S. PATENT DOCUMENTS

| | | | |
|---|---|---|---|
| D. 187,526 | 3/1960 | Hansen | D24/104 |
| D. 201,497 | 6/1965 | Ninger | D24/103 |
| D. 274,846 | 7/1984 | Eoga | D24/101 |
| 462,990 | 11/1891 | Oppenheimer | 424/451 |
| 671,804 | 4/1901 | Metcalf | 424/478 |
| 710,060 | 9/1902 | Kahn | 424/454 |
| 730,643 | 6/1903 | Hance | 424/454 |
| 1,087,843 | 2/1914 | Smith | 424/6 |
| 1,148,621 | 8/1915 | Planten | 424/7.1 |
| 2,196,283 | 4/1938 | Zick et al. | 424/455 |
| 2,410,110 | 10/1946 | Taylor | 424/478 |
| 2,757,124 | 7/1956 | Wolff | 424/481 |
| 3,444,290 | 5/1969 | Waie | 424/4 |
| 3,536,074 | 10/1970 | Aufhauser | 424/451 |
| 3,592,945 | 7/1971 | Engelking | 428/35.7 |
| 3,832,458 | 8/1974 | Merrill | 424/424 |
| 3,959,540 | 5/1976 | Leiberich et al. | 428/35.7 |
| 3,976,764 | 8/1976 | Watanabe et al. | 424/451 |
| 4,058,122 | 11/1977 | Theeuwes et al. | 424/427 |
| 4,138,013 | 2/1979 | Okajima | 206/528 |
| 4,154,636 | 5/1979 | Motoyama et al. | 424/463 |
| 4,292,304 | 9/1981 | Barels et al. | 424/456 |
| 4,439,197 | 3/1984 | Honda et al. | 604/891.1 |
| 4,578,075 | 3/1986 | Urquhart et al. | 604/892.1 |
| 4,681,583 | 7/1987 | Urquhart et al. | 424/454 |
| 4,684,524 | 8/1987 | Eckenhoff et al. | 424/469 |
| 4,717,567 | 1/1988 | Wu et al. | 424/462 |
| 4,732,915 | 3/1988 | Ayer et al. | 514/567 |
| 4,743,247 | 5/1988 | Wong | 604/892.1 |
| 4,743,248 | 5/1988 | Bartoo et al. | 604/892.1 |
| 4,773,907 | 9/1988 | Urquhart et al. | 424/467 |
| 4,774,092 | 9/1988 | Hamilton | 424/453 |
| 4,795,644 | 1/1989 | Zentner | 424/468 |
| 4,820,524 | 4/1989 | Berta | 424/475 X |
| 4,822,618 | 4/1989 | Schweiger et al. | 424/453 |
| 4,886,668 | 12/1989 | Haslam et al. | 424/424 |
| 4,973,480 | 11/1990 | Hermelin et al. | 424/454 |
| 4,978,521 | 12/1990 | Blue | 424/7.1 |
| 5,089,270 | 2/1992 | Hampton et al. | 424/465 |

OTHER PUBLICATIONS

The Theory of Practice and Industrial Pharmacy, pp. 374–401, 3rd ed., Lea & Febiger, Philadelphia, Pa. (1986).
CapsuleNews, vol. 1, No. 1, pp. 1–4, Warner–Lambert Company, 1991.
Elanco Qualicaps brochure, (F6.200).

Primary Examiner—Thurman K. Page
Assistant Examiner—Robert H. Harrison
Attorney, Agent, or Firm—Burns, Doane, Swecker & Mathis

[57] ABSTRACT

The invention relates to a method for making and administering a blinded oral dosage form and the blinded oral dosage form therefor, used for disguising the identity of tableted medications. The method includes making a blinded oral dosage form by placing a tableted medication within a capsule have a diameter greater than its height. The blinded oral dosage form is the combination of the above-described capsule and the tableted medication.

5 Claims, 3 Drawing Sheets

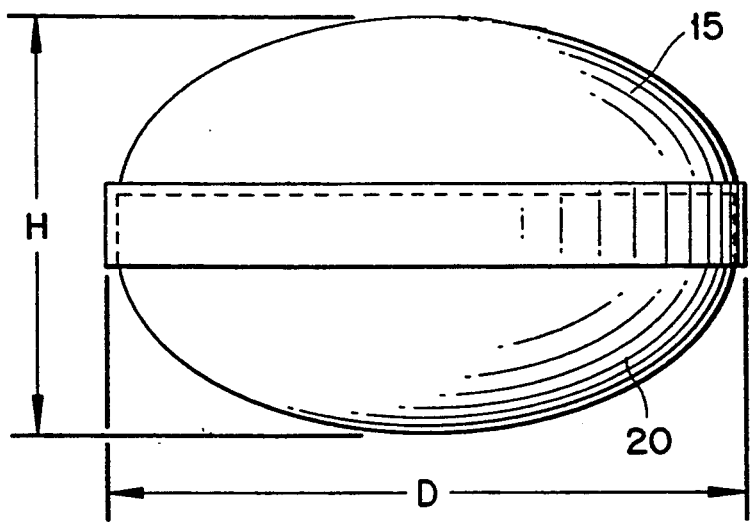
FIG. 1
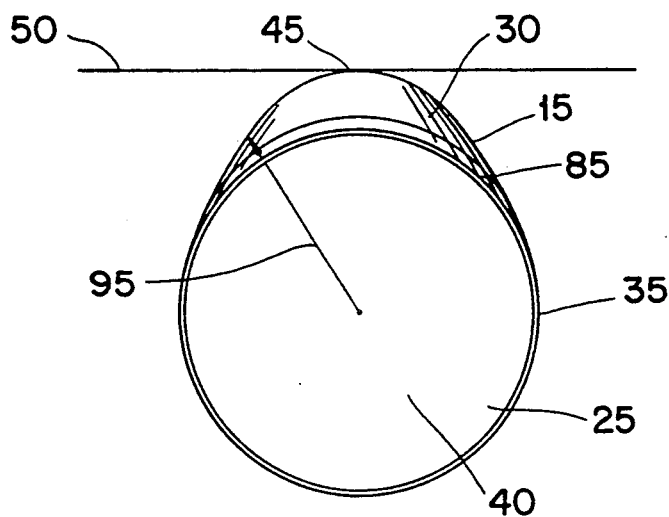
FIG. 2
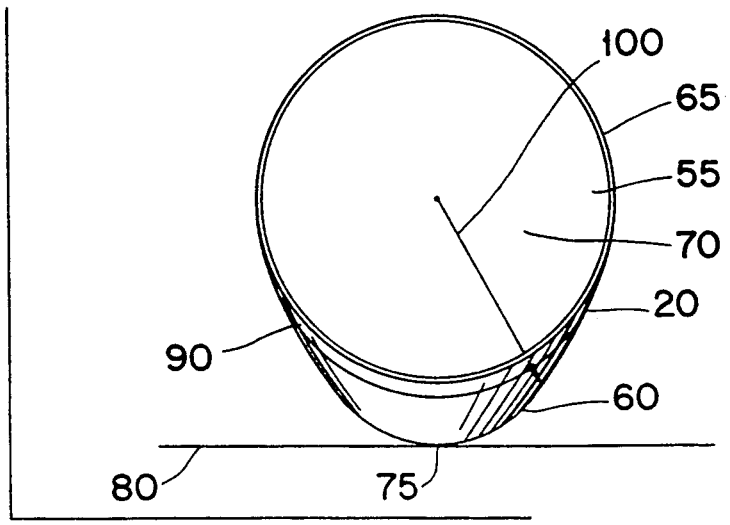

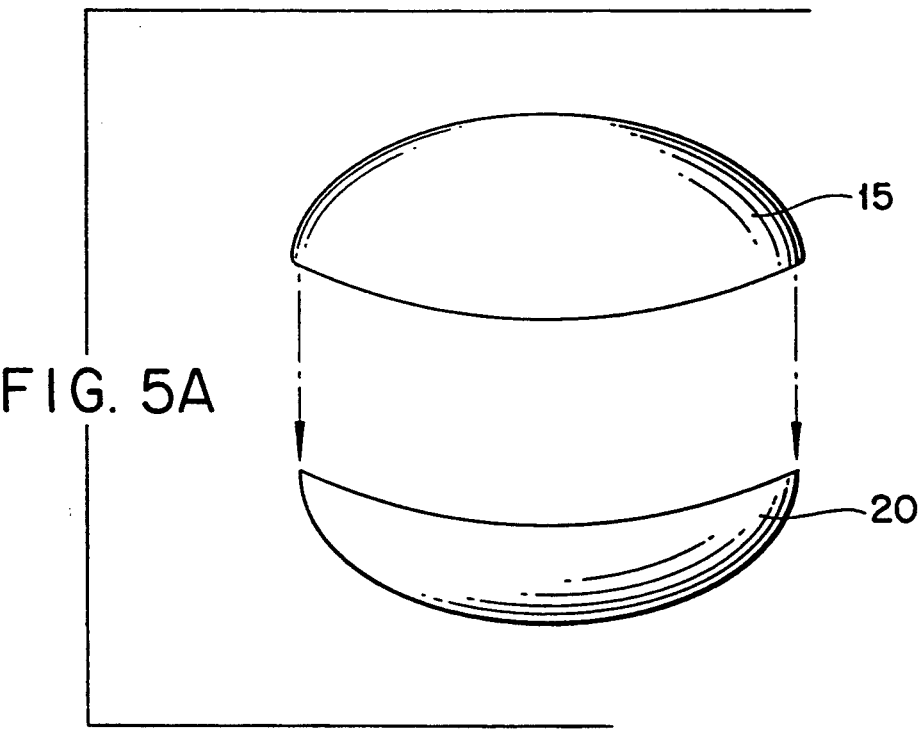
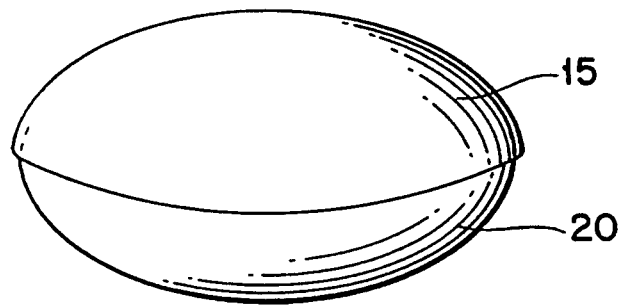

METHODS FOR MAKING AND ADMINISTERING A BLINDED ORAL DOSAGE FORM AND BLINDED ORAL DOSAGE FORM THEREFOR

BACKGROUND OF THE INVENTION

1. Field of the Invention

The present invention relates to a method for making and administering a blinded oral dosage form and the blinded oral dosage form therefor, used for disguising the identity of tableted medications.

2. Description of the Prior Art

Over the years, various methods and devices have been used to compare one medication with another to determine the relative safety and/or efficacy of the medication. It is a common practice to disguise the medications in order to prevent any prejudice from investigators administering the drugs and subjects ingesting the drugs. Disguising medications from investigators administering or subjects ingesting the medication is commonly referred to as "blinding".

Tableted medications are normally "blinded" by placing the medication in elongated cylindrical, i.e., tubular, opaque gelatin capsules along with inactive packing materials. In this way, none of the tableted medications can be identified by the investigators administering the medication or subjects ingesting the medication. However, conventional "blinding" procedures using elongated cylindrical gelatin capsules have specific limitations when using certain tablets since the diameter of the tablet is often very large in relation to the diameter of the capsule.

Elongated cylindrical, or tubular, gelatin capsules may be purchased in standard sizes having a body portion and a cap portion. The capsules typically have an elongated cylindrical shape with rounded ends that facilitate the swallowing of the capsule. Standard elongated cylindrical capsules may be purchased in various sizes. However, the diameter of the capsule is typically small in relation to the length or height of the capsule.

For example, ELANCO Qualicaps TM, which are typical of the industry, are available in the following sizes: 000, 00, 0EL, 0, 1, 2, 3, 4 and 5. The dimensions of these capsules are provided in the following table.

vestigating or comparing medications, one of which is in a tablet form, the investigator must obtain a capsule large enough to facilitate the diameter of the largest tablet used in the study. That is, the cylindrical or tubular capsule into which the tableted medication must be placed for purposes of blinding, must have a larger diameter than the diameter of the tablet. Alternatively, the tableted medication must be broken into small pieces or particles to place the medication into the capsule.

A standard elongated capsule having a diameter larger than the diameter of the tableted medication has a length at least two times longer than the diameter of the tableted medication. For example, a tableted medication having a diameter of 9 millimeters would have to be encapsulated in an 000 ELANCO Qualicap TM. The fill length of the ELANCO Qualicap TM is 26.1 millimeters. Consequently, the standard elongated cylindrical capsules are much longer than necessary.

One concern that arises with respect to the ingestion of medication is that the elongated cylindrical capsules large enough to encapsulate various tableted medications are so large that they are not as easily swallowed as the tableted medication itself. This is especially important when administering such medication to infants, children and the elderly who often have difficulty swallowing medication.

Another concern that arises with respect to the ingestion of medication is that elongated cylindrical capsules can accidently be swallowed sideways which causes the capsule to enter the esophagus lengthwise. This produces difficulty in swallowing and significant discomfort to the subject ingesting the capsule. This is especially important when cylindrical-shaped capsules are presented to animals as it is sometimes necessary to push the capsule down the throat of the animal.

Another concern that arises with respect to the ingestion of medication is that there are no readily available cylindrical capsules that may be used to encapsulate tableted medications having a large diameter. For example, a tableted medication having a diameter of 10 millimeters or more could not be encapsulated in even the largest ELANCO Qualicap TM which has a diameter of 9.5 millimeters. Tableted medications having a

| DIMENSIONS OF ELANCO QUALICAPS TM | | | | |
|---|---|---|---|---|
| SIZE | CAP DIAMETER (MM) | BODY DIAMETER (MM) | CAP LENGTH (MM) | BODY LENGTH (MM) | FILL[1] LENGTH (MM) |
| 000 | 9.88 | 9.5 | 13.1 | 22.0 | 26.1 |
| 00 | 8.51 | 8.15 | 11.7 | 20.2 | 23.5 |
| 0EL | 7.63 | 7.33 | 12.0 | 20.7 | 24.0 |
| 0 | 7.63 | 7.33 | 10.9 | 18.5 | 21.8 |
| 1 | 6.90 | 6.62 | 9.7 | 16.5 | 19.5 |
| 2 | 6.35 | 6.07 | 8.9 | 15.1 | 17.8 |
| 3 | 5.82 | 5.56 | 7.9 | 13.3 | 15.8 |
| 4 | 5.32 | 5.06 | 7.2 | 12.3 | 14.5 |
| 5 | 4.9 | 4.67 | 6.0 | 9.1 | 11.7 |

[1]FILL LENGTH is the recommended filled joined length of ELANCO POSILOK TM capsules which is controlled by the location of the locking features on the cap and body.

As listed, such capsules have a length to diameter ratio of well over two but less than three.

In contrast, tableted medications commonly used in the pharmaceutical industry are manufactured in various shapes and sizes. One common shape used for tableted medications is the disk-shaped tablet. The diameter of these tablets is usually large in relation to the length or height of the tablet. Consequently, when indiameter of 10 millimeters or more are common. Such medications are illustrated in the *Physician's Desk Reference*, 43rd Edition, Medical Economics Company, Inc., Oradell, N.J. (1989) and in *The Family Physician's Compendium of Drug Therapy*, McGraw-Hill Book Company, New York (1988) both of which contain actual size, full-color reproductions of various medications available from various manufacturers.

Of course, tableted medications could be broken into smaller pieces or used in smaller sizes; however, breaking tableted medications or using them in smaller sizes affects the actual kinetics of medication. In particular, when tablets are broken up into smaller sizes there is more surface area for dissolution and absorption of the medication. Furthermore, many tableted medications have various coatings which will become ineffective if destroyed. Consequently, the integrity of the investigation or comparison is compromised when breaking up the tableted medications.

Thus, in the majority of research studies, a "double-dummy" approach is used when encapsulation is not practical. The "double-dummy" approach could best be exemplified in a study in which two or more tablets of varying size (for instance, one large and one small) are compared for safety or efficacy. When the larger of two tablets is of too great a diameter to be placed inside the standard elongated capsule, it becomes necessary to produce placebos for both the large and small tablets. The "double-dummy" procedure requires the subject to ingest two tablets (one active and one placebo). Therefore, when taking a large tablet as active medication, the subject must also take a smaller tablet as a placebo and vice versa. This method allows the investigator and the subject taking the medicine to be blinded as to whether the larger tablet is an active medication or, alternatively, a placebo.

Many variations of the "double-dummy" procedure exist. However, all variations require the expense of developing placebos identical to test medications or obtaining the placebo from the manufacturer of the active product. Furthermore, it should be noted that the use of two or more tablets in a "double-dummy" procedure requires the subject to ingest several pills at each dosing period. The ingestion of two or more pills inherently results in a significant placebo effect which may increase (or, alternatively, decrease) the perceived efficacy (or side effect) profile of the study medication. In addition, ingesting multiple pills may affect the actual kinetics of the study medication.

While various unconventionally shaped capsules are known in the art, the capsules are either not used to blind tableted medications and/or are not convenient for blinding tableted medications. Such various unconventionally shaped capsules are disclosed in U.S. Pat. Nos. 462,990; 710,060; 730,643; 1,087,843; 1,148,621; 2,196,283; and 4,774,092.

U.S. Pat. No. 462,990 discloses a capsule consisting of a soluble shell or casing formed integrally with a soluble partition to provide separated chambers for different kinds of medicine. This patent does not disclose a method for blinding tableted medications. In fact, the capsules are not suitable for blinding tableted medications since they are not constructed in a manner that permits tableted medication of various sizes and shapes to be placed therein.

U.S. Pat. No. 710,060 discloses a capsule in which one piece is provided with a double wall construction and the other piece a single wall construction. The patent mentions nothing with respect to placing a tableted medication within the capsule.

U.S. Pat. No. 730,643 discloses a tableted medication contained within a gelatin casing. The tableted medication is enclosed within the casing along with a liquid ingredient for introducing the solid and liquid simultaneously. The device shown in U.S. Pat. No. 730,643 is not acceptable for blinding procedures since the casing containing the liquid and solid ingredients is formed with various presses and dies resulting in an integrally formed-one piece sphere.

U.S. Pat. No. 3,536,074 discloses a tableted medication within a liquid impervious frangible sac. The tableted medication is enclosed within the frangible sac along with a liquid ingredient to assist in the swallowing of the tableted medication. The device shown in U.S. Pat. No. 3,536,074 is not acceptable for blinding procedures since the frangible sac containing the liquid and solid ingredients is an integrally-formed one piece unit.

The devices disclosed in U.S. Pat. Nos. 730,643 and 3,536,074 are unacceptable for blinding studies since the manufacture of such devices requires manufacturing equipment for placing the tablet and liquid within the capsule and for sealing the capsule.

The above-described methods and devices are intended to provide a means for "blinding" medications from investigators and subjects taking the medications. However, as described above, there are many disadvantages associated with these methods. Such disadvantages include the fact that elongated cylindrical or tubular shaped capsules readily available to those in the art are not convenient for disguising many tableted medications due to their inability to contain many of the larger tableted medications and the unsatisfactory nature of the alternative methods which are commonly utilized.

Thus, there remains a long felt need in the art for an improved method and device for "blinding" tableted medications containing an active substance. Such method would facilitate the investigation of various medications to determine their physiological or pharmacological effect as well as to compare the safety and/or efficacy of the medications with other medications.

SUMMARY OF THE INVENTION

It is, therefore, a primary object of the present invention to provide an improved method for conducting a blinded study, an improved method for blinding a tableted medication and an improved dosage form comprising a tableted medication within a capsule such that investigators analyzing such dosage form and subjects ingesting such dosage form cannot determine the identity of the medication they are administering or ingesting.

Another object of the present invention is to provide a method for coating a tableted medication by encapsulating the tableted medication in a capsule More readily adapted for tableted medications. The method allows researchers and pharmacists to provide medications with one or more desirable coatings without having to specially order the tableted medication with the desired coating.

Still another object of the present invention is to provide a covering for a tableted medication without the need for special coating equipment, i.e. a capsule having a shape that can be more readily swallowed than a conventional capsule that is large enough to encapsulate the tableted medication.

Yet another object of the present invention is to provide a method for coating a capsule with conventional tablet coating apparatus and by conventional tablet coating procedures.

Still another object of the present invention is to provide a capsule having a shape that can be more readily swallowed than a conventional capsule that is large enough to "encapsulate" a large tablet. The blinded oral dosage form of the present invention does not need to be significantly larger than the tablet itself, in both diameter and thickness, and could therefore be as easily swallowed as the tablet itself. Thus, the blinded oral dosage form of the present invention may be transported through the esophagus more easily than a readily available elongated cylindrical capsule that would be required to disguise the same tablet.

Consequently, another object of the present invention is to provide a blinded oral dosage form that is more easily swallowed by people who experience difficulty in swallowing capsules than a readily available elongated cylindrical capsule that would be required to disguise the same tablet.

Another object of the present invention is to provide a blinded oral dosage form that could be used for blinding conventional Medications and which is resistant to tampering.

The method for conducting a blinded study comprises making a first blinded oral dosage form by placing a first composition within a capsule having a body portion and a cap portion such that the diameter of the capsule is greater than its height when closed. The Method also includes making a second blinded oral dosage form by placing a second composition within a substantially identical capsule and then closing the capsule. The method also includes administering the first blinded oral dosage form to a subject and administering the second blinded oral dosage form to the same subject or to another subject.

Accordingly, the method for blinding a tableted medication comprises placing the tableted Medication within a capsule having a body portion and a cap portion such that the diameter of the capsule is greater than or equal to its height when closed.

Specifically, the method for blinding a tableted medication comprises placing the tableted medication within a capsule having a body portion and cap portion and then closing the capsule, wherein the body portion comprises an open end and an oppositely positioned closed end. The open end is defined by a circumferential edge lying in a first plane. The body portion is configured such that the greatest straight line distance connecting two points on the circumferential edge is greater than the perpendicular distance between the first plane and a second plane which contacts an outer surface of the closed end of the body portion and which is parallel to the first plane. Preferably, the cap portion is configured similarly to the body portion. Even more preferably, the method includes the use of a cylindrical capsule having interlocking cylindrical body and cap portions.

The dosage form of the present invention comprises a capsule and, within the capsule, a tableted medication. The capsule has an interlocking body portion and cap portion and a diameter greater than its height when closed.

More specifically, the dosage form comprises a capsule and, within the capsule, a tableted medication, wherein the capsule comprises an interlocking body portion and cap portion. The body portion comprises an open end and an oppositely positioned closed end. The open end is defined by a circumferential edge lying in a first plane. The body portion is configured such that the greatest straight line distance connecting two points on the circumferential edge is greater than the perpendicular distance between the first plane and a second plane which contacts an outer surface of the closed end of the body portion and which is parallel to the first plane. Preferably, the cap portion is configured similarly to the body portion. Even more preferably, the dosage form comprises a capsule and, within the capsule, a tableted medication, wherein the capsule comprises interlocking cylindrical body and cap portions.

Even more specifically, the dosage form of the present invention comprises the combination of a tableted medication and a capsule, the capsule including a body portion and a cap portion. The cap portion and the body portion each are hollow and have an open end with means which interfit with one another so that the body portion and the cap portion can be brought towards one another along an axis with their open ends facing one another and connected to one another to define the capsule. The capsule has a cavity formed by the hollow body portion and the hollow cap portion and the tableted medication is disposed within the cavity. The capsule has a length or height as measured along the axis and a diameter as measured perpendicular to the axis, the height Of the capsule being less than the diameter of the capsule as measured from an outer surface Of the capsule.

BRIEF DESCRIPTION OF THE DRAWINGS

The features of the present invention will become apparent from the description, considered in conjunction With the drawings, in which like elements bear like reference numerals and wherein:

FIG. 1 is a perspective view of one embodiment of the capsule of the blinded oral dosage form of the present invention illustrating the capsule;

FIG. 2 is a perspective view of the capsule shown in FIG. 1 illustrating two portions of the capsule separated from one another;

FIG. 5 is a perspective view of another embodiment of the blinded oral dosage form employing a different form of interlocking mechanism for interlocking the two portions.

DETAILED DESCRIPTION OF THE PREFERRED EMBODIMENTS OF THE INVENTION

Figure 3:
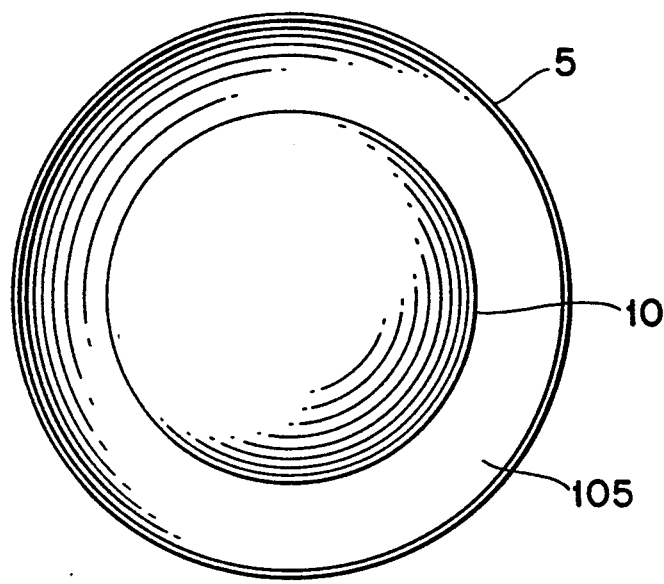
FIG. 3 is a cross-sectional view of the embodiment of the blinded oral dosage form illustrated in FIG. 1 with a tableted medication enclosed within the capsule.

The following description of various embodiments of the dosage form, methods of making the dosage form and methods of administering the dosage form are merely illustrative of the present invention and they should not be considered as limiting the scope of the invention in any way, as these illustrations and other equivalents thereof will become more apparent to those versed in the art in the light of the present disclosure, and the accompanying claims.

The method for conducting a blinded study comprises making a first blinded oral dosage form by placing a first composition within a capsule having a body portion and a cap portion such that the diameter of the capsule is greater than its height when closed. The method also includes making a second blinded oral dosage form by placing a second composition within a substantially identical capsule and then closing the capsule. The method also includes administering the first blinded oral dosage form to a subject and administering the second blinded oral dosage form to the same subject or to another subject.

Accordingly, the Method for blinding a tableted medication comprises placing the tableted medication within a capsule having a body portion and a cap portion such that the diameter of the capsule is greater than its height when closed.

The blinded oral dosage form of the present invention includes a capsule having a body portion and a cap portion which interlock to form an enclosed space or cavity referred to herein as the volume of the capsule. Prior to interlocking the cap portion with the body portion, one or more tableted medications are placed within the body portion along with any desired non-toxic, pharmaceutically acceptable filler material sufficient to prevent substantial movement of the tablet with the capsule. Optionally, only non-toxic, pharmaceutically acceptable filler material is placed with the capsule to form a placebo. Once the tablet or tablets and/or filler material is placed inside the body portion and the cap portion is interlocked with the body portion, the tablet or tablets and/or the filler material is blinded to persons administering and subjects ingesting the blinded oral dosage form.

Referring initially to FIG. 1, the capsule includes a cap portion 15 and body portion 20 of the blinded oral dosage form of the present invention produced in such a way to allow the cap portion 15 and body portion 20 to be combined by fitting the one into the other with sufficiently close tolerances to produce what is essentially a friction lock.

Generally, the capsule comprises a cross-sectional dimension D and a height or length R. The cross-sectional dimension D, when the capsule has a circular cross-section surface, is the diameter of the cross-section. In instances where the cross-sectional surface is not circular, the cross-sectional dimension D is the greatest straight line distance connecting two points on the edge of the cross-sectional surface. Preferably, however, the cross-sectional surface is circular. Nonetheless, as used herein, the term "diameter" is the greatest straight line distance connecting two points on the edge of the cross-sectional surface. This distance is also referred to herein as the cross-sectional dimension D. The height or length H is the distance from the top of the capsule to the bottom of the capsule in a direction perpendicular to the cross-sectional dimension D. Preferably, the cross-sectional dimension D is greater than the height or length R, preferably much greater.

As shown in FIG. 2, the cap portion 15 comprises an open end 25 and an oppositely positioned closed end 30. The open end is defined by a circumferential edge 35 which lies in a first plane 40. Opposite the open end 25, there is a closed end 30 having a point or surface 45 touching but not intersecting a second plane 50 which is parallel to the first plane 40. The greatest straight line distance connecting any two points on the circumferential edge 35 is greater than the perpendicular distance between the first plane 40 and the second plane 50. That is, the cross-sectional dimension D is greater than the height H of the cap portion is.

Likewise, the body portion 20 comprises an open end 55 and an oppositely positioned closed end 60. The open end is defined by a circumferential edge 65 which lies in a first plane 70. Opposite the open end 55 there is a closed end 60 having a point or surface 75 touching but not intersecting a second plane 80 Which is parallel to the first plane 70. The greatest straight line distance connecting any two points on the circumferential edge 65 is greater than the perpendicular distance between the first plane 70 and the second plane 80. That is, the cross-sectional dimension D is greater than the height u of the body portion 20.

Tablets of various sizes and shapes along with sufficient non-toxic, pharmaceutically acceptable filler material (to avoid the tablet rattling within the capsule) may be placed within cap 15 or body 20 portions; however, the largest tablet must be minimally smaller than the respective opening in order for the tablet to be placed within the capsule. Optionally, only non-toxic, pharmaceutically acceptable filler material is placed within a capsule to form a placebo. In addition, various powdered medications or liquid medications could be placed within a capsule to form a comparative dosage form.

Normally, for human applications, tablets have a diameter ranging from about 2 to about 16 millimeters, preferably about 5 to about 12 millimeters, with a thickness ranging between about 1 and about 10 millimeters, preferably about 2 to about 7 millimeters.

Thus, for human applications, it is contemplated that the cross-sectional dimension D, i.e., the greatest straight line distance between two points on the circumferential edge of the cap or body portions of the capsule, could range from about 3 to about 18 millimeters, preferably about 3 to about 13 millimeters. In addition, it is contemplated that the overall length or height H of the capsule, i.e., the distance between the point or surface 45 touching the second plane of the cap and the point or surface 75 touching the second plane of the body when the body and cap are interlocked, could range from about 3 to about 11 millimeters, preferably about 3 to about 7 millimeters. However, the cross-sectional dimension D should be greater than or equal to the length or height H. Preferably, the cross-sectional dimension D is greater than the length or height H. Even more preferably, the cross-sectional dimension D is at least 1.5 times greater than length or height H. Most preferably, the cross-sectional dimension D is at least 2.0 times greater than the length or height H.

Another preferred embodiment of the invention for human applications would have a diameter D between about 4 and about 14 millimeters and a height or length H between about 3 and about 8 millimeters. In this way, tablets of normal size (3 to 13 millimeters in diameter and 2 to 7 millimeters in thickness) may be contained within the blinded oral dosage, allowing for packing materials to avoid movement of the tablet within the device.

Another preferred embodiment of the blinded oral dosage of the present invention includes a capsule having a diameter D that is larger than the diameter of the standard elongated cylindrical capsules. Specifically, this preferred embodiment has a diameter of at least about 10 millimeters, or even a capsule having a diameter of at least about 11 or about 12 millimeters. Such preferred capsules are particularly suitable for encapsulating tableted medications having a diameter larger than the diameter of standard elongated cylindrical capsules. Tableted medications having a diameter of at least 10 millimeters include the 400 mg dosage of Motrin® brand ibuprofen tablets, the 500 mg dosage of Maximum Strength Anacin® brand analgesic (aspirin/caffeine) tablets, the 250 mg dosage of Wyamycin®S brand erythromycin stearate tablets, the 500 mg dosage of Aralen ® Phosphate brand chloroquine phosphate tablets, the 500 mg dosage of Tolinase ® brand tolazamide tablets as well as many other widely available medications. Other tableted medications having a diameter of at least 10 millimeters are illustrated in the *Physician's Desk Reference,* 43rd Edition, Medical Economics Company, Inc., Oradell, N.J. (1989) and in *The Family Physician's Compendium of Drug Therapy,* McGraw-Hill Book Company, New York (1988) both of which contain actual size, full-color reproductions of various medications available from a variety of manufacturers.

The device illustrated in FIG. 2 further includes a female friction portion 85 for placing on top of and interlocking with the male friction portion 90 of the body portion of the device. The female friction portion 85 of the device for the above-described human applications may be between about 1 and about 10 millimeters long, preferably between about 1 and about 5 millimeters long. The male friction portion 90 of the device may have dimensions similar to that of the female friction portion 85.

As shown, the cap portion 15 and the body portion 20 of the capsule may have rounded closed ends. The radius 95 of the cap portion or the radius 100 of the body portion of the device may be, for human applications, between about 1 and about 9 millimeters. The radius is the distance from the midpoint of the area defined by the circumferential edge to the inside surface of the closed end of the respective portion. The radius is not uniform in most instances from the midpoint of the area defined by the circumferential edge to various points on the inside surface of the closed end. That is, the distance from the midpoint to one point on the inside surface may not be the same as the distance from the midpoint to a different point on the inside surface. Rounded closed ends are preferred to facilitate ease of swallowing.

FIG. 3 shows a top view with midline cut-away illustrating a cylindrical or disk-shaped blinded oral dosage form complete with the tablet 10 contained within the capsule 5. As shown, there may be a certain amount of space 105 within the cavity formed by interlocking the cap portion and body portion for placement of the non-toxic, pharmaceutically acceptable filler material. The filler material may keep the tablet from rattling inside the capsule and giving away its existence. Optionally, only non-toxic, pharmaceutically acceptable filler material is placed within the capsule to form a placebo.

A preferred distance from the edge of the tablet to the inside edge of either the cap or the body portion of the device for the above-described devices suitable for human applications may be from about 0.1 to about 6 millimeters. Preferably, one or more tablets occupy at least 20 percent of the enclosed space or cavity of the capsule. More preferably, one or more tablets occupy at least 35 percent of the enclosed space of the capsule. Even more preferably, one or more tablets occupy at least 50 percent of the enclosed space of the capsule. Even more preferably, one or more tablets occupy at least 75 percent of the enclosed space. Even more preferably, one or more tablets occupy at least 90 percent of the enclosed space.

As the two parts of the capsule are placed together (covering the contents), the friction produced by the close tolerances between the two segments should be sufficient to keep the parts from disassociating during transportation and normal use. In addition, it should be sufficiently difficult to open the product to inhibit research subjects or investigators from attempting to determine the contents.

While the above-described illustrations describe preferred embodiments of the blinded oral dosage of the present invention, it should be noted that the device may be of any shape and size. Thus, the circumferential edge of either the cap portion or body portion of the capsule could be circular, ellipsoidal, square, rectangular, triangular or any other circumferential multi-sided shape as well as any other circumferential curvilinear shape. Likewise, while the above illustrations show rounded closed ends of the cap portion and the body portion, the closed ends could have flat surfaces.

Most preferably, the capsules of the present invention are of a cylindrical or disk shape with rounded ends. However, by use of the term "cylindrical", when referring to the capsules of the present invention, it is meant that the capsules when assembled are "non-elongated". The phrase "non-elongated" when referring to the preferred cylindrical devices of the present invention, means that the diameter D of the device is greater than or equal to the length or height H, i.e., the straight line distance from end point to end point, of the capsule. More specifically, the preferred blinded oral dosage of the present invention has a non-elongated cylindrical shape wherein the ends of the cylinder are rounded or without edges as illustrated in FIGS. 1-5. In contrast, commercially available capsules are elongated. That is, the length or height of commercially available capsules is greater than the diameter. Typically, the length to diameter ratio of commercially available capsules is between two and three.

Thus, as used herein, an "elongated cylindrical shape" refers to the shape of standard cylindrical capsules widely used in manufacturing encapsulated medications. Such standard elongated cylindrical shaped capsules typically have rounded ends and have a length or height longer than its diameter. Examples of medications available in capsules having an elongated cylindrical shape include THEOBID ® capsules, TRINSICON ® capsules, VICONFORTE ® capsules, AMOXIL ® capsules, BACTOCILL ® capsules, CLOXAPEN ® capsules, DYCILL ® capsules, TIGAN ® capsules, DECONAMINE ® capsules, MEXITIL ® capsules, R-TUSS° capsules, MIDRIN ® capsules, ACTIFED ® capsules, SUDAFED° capsules, ZOUIRAX ® capsules, BRONTRIL ® capsules, HYDROCET ® capsules and MIDRIN ® capsules. Each of the above-listed capsules as well as others are available via various manufacturers as set forth in the *Physicians Desk Reference,* 43rd Edition, Medical Economics Company, Inc., Oradell, N.J. (1989).

The widely available elongated cylindrical capsules are also shown in *Remington's Pharmaceutical Sciences,* 18th Edition, on Page 1658 at FIG. 89-34, Mack Publishing Company, Easton, Pa. (1990).

The widely available elongated cylindrical capsules are also available empty and ready for filling. Elongated cylindrical capsules available empty and ready for filling include the ELANCO QUALICAPS ™ referred to above.

In contrast to the elongated cylindrical capsules, the capsules of the present invention have a length (i.e. height) to diameter ratio less than or equal to one. Nonetheless, the dimensions of the blinded oral dosage of the present invention may be of any size depending on the application, just so long as the height to diameter ratio does not exceed one. For example, when administering the blinded oral dosage of the present invention to large animals, such as cattle or horses, larger dosage forms may be required. Of course, logic dictates that the size of the blinded oral dosage form depends both on the size of the tablet and the size of the subject ingesting the dosage. Thus, any variety of sizes are applicable to the present invention. However, the cross-sectional dimension D should be greater than or equal to the length or height H. Preferably, D is greater than the height H.

The tablets placed within the enclosed cavity of the blinded oral dosage form of the invention may be any one of a wide variety of tableted medications. Tableted medications are medications that have been pressed or otherwise formed into a solid dosage form ready for ingestion. The tableted medication may be any number of a wide variety of shapes currently available to those skilled in the art. In this regard, manufacturers of tableted medications manufacture such tablets in round or cylindrical shapes, square shapes, rectangular shapes, triangular shapes, oval shapes, spherical shapes, hexagonal shapes, trapezoidal shapes, etc. Accordingly, any such tablet or tablet shape is suitable for placing within the cavity of the blinded oral dosage form.

When the cap portion is engaged with the body portion of the instant dosage form, an enclosed cavity is formed such that the contents of the device are not exposed to external elements present during transportation and handling of the dosage forms. The volume of the capsule is the enclosed cavity formed by the cap and body portions of the capsule. The cap portion may engage the body portion via any locking mechanism known in the art. Locking mechanisms are particularly important in research studies as they inhibit volunteers (as well as researchers) from opening capsules and discovering their contents prior to administration. They are also important in simply keeping the two halves of the product from falling apart during storage, transportation or usage.

Locking mechanisms may include, for example, friction-type locking mechanisms as shown in FIGS. 1 and 2. The friction-type locking mechanism includes friction produced by the close tolerance between the male and female segments of the capsule.

Figure 4:
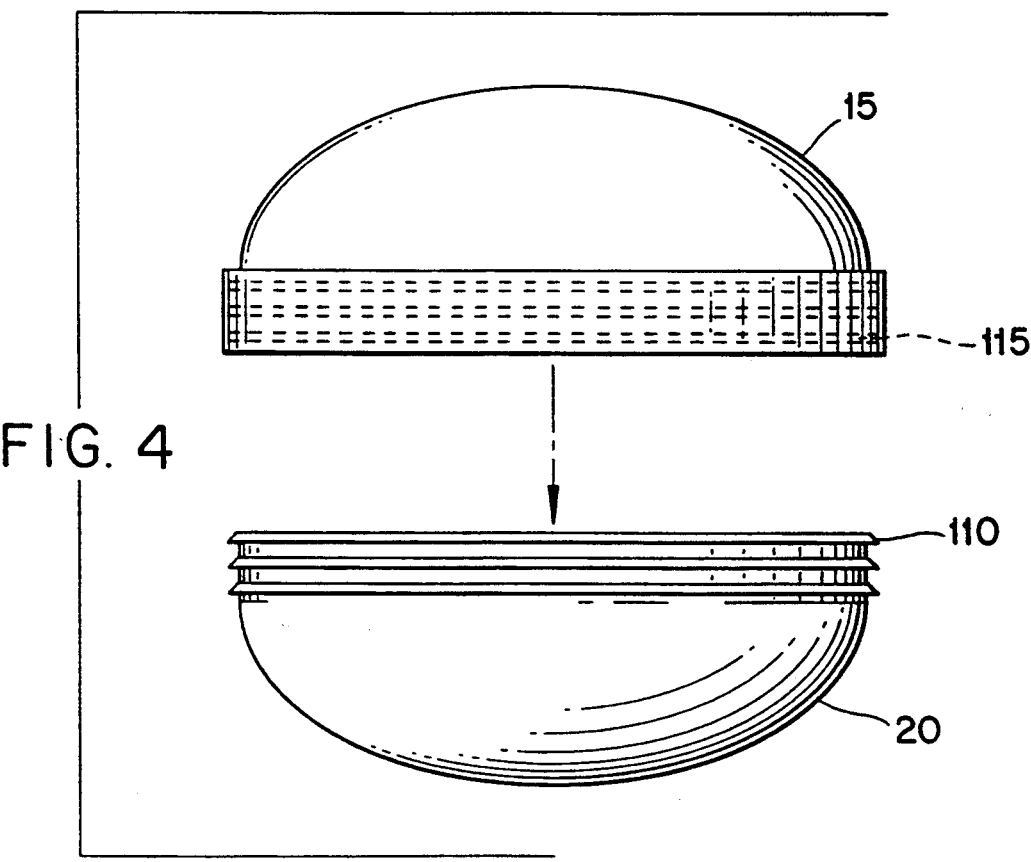
FIG. 4 is a perspective view of another embodiment of the blinded oral dosage form employing a different form of interlocking mechanism for interlocking the two portions.

FIG. 4 is an illustration of another embodiment of the blinded oral dosage form showing a tongue and groove locking mechanism. In this configuration, the body portion 20 of the device has accordion-shaped ridges 110 permitting it to move into the cap portion 15 of the device such that it interlocks with one or more internal indentations 115. As shown, one or more internal indentations 115 or ridges 110 may be used. Optionally, the cap portion could contain the ridges and the body portion could contain the internal indentations of the locking mechanism.

If the male section has two or more internal indentations or ridges, any one of the ridges could be locked onto depending on the thickness of the tablet contained inside. This would allow the tablet-shaped capsule to have one, two or more thicknesses to accommodate tablets of various thickness or even multiple tablets being encapsulated within the product. Obviously, for any given study, all tablet-shaped capsules would be of identical thickness, with more or less filler present depending upon the space occupied by the tablet(s) encapsulated.

The cross-section of the ridges or the internal indentation may have a profile which is curved or angular, and may range in shape, for example, from a single to a multiple radius design, or from a V-shape to a multi-angular shape, such as for example a square, rectangular, trapezoidal, etc. shapes. Examples of such tongue and groove-type locking mechanisms are illustrated in U.S. Pat. No. 4,882,618.

As with the "tongue and groove" and "friction" locking mechanisms, a "flexible lip" could also be used as a means of maintaining the integrity of a tablet-shaped capsule as described above. FIG. 5 provides an illustration of another embodiment of the oral dosage form of the invention containing a flexible lip type locking mechanism. In this form, the cap portion 15 of the device would fit over the body portion 20 of the device or vice versa. Both the cap and body portions of the device contain a portion of the "flexible lip" locking mechanism. Each portion of the locking mechanism is rounded on the edge in such a way as to allow the body portion 20 of the locking mechanism (which is slightly smaller) to slip into the cap portion 15 of the locking mechanism. The larger rounded edge of the cap portion 15 of the locking mechanism is sufficiently flexible to expand and slip over the smaller but similarly rounded edge of the body portion 15 of the locking mechanism and due to the overlap, lock both segments together.

Additional locking mechanisms could include screw-type locking mechanisms and external fasteners. Accordingly, any locking mechanism in existence for standard capsule shapes could be utilized for the blinded oral dosage of the present invention as long as it insures the integrity of the dosage form during normal handling.

Additionally, it is noted that each of the above-mentioned locking mechanisms may allow locking of the capsules at various thicknesses so tablets of various thicknesses could be encapsulated along with fillers.

The blinded oral dosage form may also include various wraps or tapes conventionally used with standard gelatin capsules to insure that the device is not tampered with prior to administration. It may be desired to apply a sealing band to an assembled dosage form, to prevent leakage in the case of any possible powder or liquid fillings, or to render the capsule tamper-evident or tamper resistant or for identification purposes. This may be achieved using known methods and equipment, such as, for example, the Quali-Seal machine (Manufacturing Chemist, January, 1987, p. 27).

Preferably, the body and cap portions of the blinded oral dosage form of the present invention are made of a hard gelatin and could be manufactured on existing equipment with modifications to dies and other parts of those or similar machines. Optionally, the capsules of the present invention could be made of soft gelatin or any other material used to make conventional capsules.

By way of illustration, hard gelatin capsules may be made in two parts by dipping stainless steel pins into a molten gelatin solution, and allowing the gelatin to set and dry. It is generally known that the gelatin film, as it dries, also undergoes shrinkage. The shrinkage depends on a number of factors such as the amount of water to be eliminated, the gelatin used, the drying regime and the number and type of additives such as dyes, other colorants, opacifiers, plasticizers, viscosity builders or surfactants which may be included within the gelatin compositions of the present invention. Such processes and compositions are well known in the art, for example, see *The Theory and Practice of Industrial Pharmacy*, 3rd Ed., Lea & Febiger, Philadelphia (1986) and *Rem-* ington's Pharmaceutical Sciences, 18th Edition, Mack Publishing Company, Easton, Pa. (1990).

In addition, the body and cap portions of the blinded oral dosage form may be made of materials that are soluble in alkaline intestinal secretions but substantially insoluble in and resistant to acid secretions of the stomach. Such materials are commonly referred to as having enteric properties. The enteric dosage forms may be made, for example, by dip-molding using a homogeneous film-forming mixture comprising (1) gelatin and an ammonium salt of hydroxypropyl methylcelluose phthalate polymer, or (2) hydroxypropyl methylcelluose and an ammonium salt of cellulose acetate phthalate polymer, or (3) gelatin and an ammonium salt of a copolymer of methacrylic acid and methacrylic acid ester optionally in combination with additional ingredients such as plasticizers, surfactants and coloring agents. The above compositions are described, for example, in more detail in U.S. Pat. No. 4,138,013.

Likewise, many other ingestible materials may be used to make the cap and body portions of the blinded oral dosage form of the present invention. Preferably, however, the capsules are made of a hard gelatin composition.

As a result of the non-elongated shape of the blinded oral dosage form, it is also suitable for coating with pharmaceutical grade materials in standard tablet coating bins (unlike a standard elongated shaped capsule which does not tumble appropriately for coating purposes). The dosage forms of the present invention may tumble exactly like a standard tablet and may thereby coat as easily as any tablet depending on the particular embodiment. Coatings (or multiple coating layers) of various degrees of hardness, thickness or solubility would be aesthetically pleasing and have standard pharmaceutical qualities regarding dissolution rate, ease of swallowing and manufacturing advantages.

Preferred embodiments of the blinded oral dosage form could be coated by a standard tablet coating process such as described, for example, in *Remington's Pharmaceutical Sciences*, 18th Edition, Chapter 90, "Coating Of Pharmaceutical Dosage Forms", Mack Publishing Company, Easton, Pa. (1990).

In addition to the above advantages, one or more coatings may provide a "tamper proof" blinded oral dosage form as opening would break the coating. The broken coating material would be difficult, if not impossible, to restore to its original character and would be an obvious signal to the investigators or subjects ingesting the device not to use the product. The break could be made more obvious in many ways including use of layered coverings of different colorings, highly friable coating materials or unusual colors. The coating could also help maintain the integrity of the product during both research and commercial use. Also, the coating may be used in conjunction with an external wrap or tamper resistant tape that protects the device. Additionally, it is also possible to utilize a number of coating compounds or active agents in the coating composition to achieve a desired effect. For instance, an enteric coating can be applied as one layer or in combination with another coating solution.

The method of the present invention includes preparing blinded tableted medications. In particular, the method includes disguising a tableted medication by placing the medication in a non-elongated capsule, i.e., a capsule of the present invention having a cross-sectional dimension D greater than or equal to its length or height H.

This method provides a means for disguising tableted medications in a capsule more readily adapted for tableted medications. Thus, standard elongated capsules which are overly large in relation to the tableted medications are not necessary. In fact, the method includes disguising one or more tablets that occupy at least 20 percent, more preferably at least 35 percent, more preferably at least 50 percent, more preferably at least 75 percent or most preferably at least 90 percent of the enclosed space or cavity of the capsule.

The method may further include placing one or more non-toxic, pharmaceutically acceptable filler materials within the cavity of the capsule to prevent the tablet from rattling inside the capsule. This prevents researchers or subjects from distinguishing between capsules containing tablets of various sizes, or between those containing tablets and those containing non-tableted medications or fillers only (i.e., placebos). Optionally, only non-toxic, pharmaceutically acceptable filler is placed within the capsules of the present invention to form a placebo. Suitable non-toxic, pharmaceutically acceptable filler material, including sugars and starches, would be apparent to those skilled in the art.

Additionally, the method may further include applying one or more coatings covering the capsule. Certain coatings may be applied either before or after the tablet is placed within the capsule. In the case wherein the capsules are precoated, the method of the present invention includes a simple and easy means for encapsulating a tableted medication to provide a desired coating without the need to coat the tablet itself. In the case wherein the capsules are coated after filling, the closed capsule, unlike standard elongated capsules, may be coated according to conventional tablet coating tumble processes and in conventional tablet coating equipment.

Furthermore, the method of the present invention is particularly suitable for comparing two different medications, i.e., one tableted medication and another medication which may or may not be tableted. Comparing two different medications would include making a first blinded oral dosage form by disguising a first tableted medication in a non-elongated capsule and making a second blinded oral dosage form by disguising a second medication (either tableted or not) in a non-elongated capsule having substantially the same size and shape as the first blinded oral dosage form.

Thus, the method of the present invention further provides a means for disguising or blinding one or more medications of different shapes and sizes, e.g., one large and one small, or even the same medication in different forms or amounts. The method in such case may include placing the large tableted medication in a capsule of the present invention of large enough size to hold the tableted medication and placing a smaller tableted medication in a capsule identical to the capsule in which the larger tableted medication was placed. In this way, the person conducting the clinical trial and the subject ingesting the blinded oral dosage would not know what medication, form of medication or amount of medication was administered. By use of this method, two medications of substantially different size or shape or the same medication in different forms or amounts could be readily compared.

The method of the present invention is also suitable for analyzing one tableted medication as compared to a second dosage form which does not contain an effective medication. Analyzing one tableted medication may include making a first blinded oral dosage form by disguising a first tableted medication in a non-elongated capsule and making a second blinded oral dosage form having substantially the same size and shape as the first blinded oral dosage that does not contain an effective medication, i.e., a placebo.

From the foregoing description, one of ordinary skill in the art can easily ascertain the essential characteristics of the instant invention, and without departing from the spirit and scope thereof, can make various changes and/or modifications of the invention to adapt it to various usages and conditions. As such, these changes and/or modifications are properly, equitably and intended to be, within the full range of equivalents of the following claims.

What is claimed is:

1. A method for blinding a tableted medication comprising placing said tableted medication within a cylindrical, ingestible capsule effective for administering a tableted medication having interlocking cylindrical body and cap portions, said body portion comprising an open end and an oppositely positioned closed end, said open end being defined by a circumferential edge, said circumferential edge lying in a first plane, said body portion being configured such that the greatest straight line distance connecting two points on said circumferential edge is greater than the perpendicular distance between said first plane and a second plane which contacts an outer surface of the closed end of the body portion and which is parallel to the first plane; and then closing the capsule.

2. The method as claimed in claim 1, wherein said cap portion comprises an open end and a closed end, said open end being defined by a circumferential edge, said circumferential edge lying in a first plane, said cap portion being configured such that the greatest straight line distance connecting two points on said circumferential edge of said body portion is greater than the perpendicular distance between said second plane of said body portion and a second plane of the cap portion which contacts an outer surface of the closed end of the cap portion and which is parallel to the first plane of the cap portion.

3. The method as claimed in claim 2, wherein said tableted medication occupies at least 35 percent of the volume of the closed capsule.

4. The method as claimed in claim 3, wherein said tableted medication occupies at least 50 percent of the volume of the closed capsule.

5. The method as claimed in claim 1, further comprising applying one or more coatings to the closed capsule.

* * * * *